United States Patent [19]

Baxter-Lowe

[11] Patent Number: 5,545,526
[45] Date of Patent: Aug. 13, 1996

[54] METHOD FOR HLA TYPING

[75] Inventor: Lee Ann Baxter-Lowe, New Berlin, Wis.

[73] Assignee: Blood Center Research Foundation, Inc., The, Milwaukee, Wis.

[21] Appl. No.: 25,038

[22] Filed: Mar. 1, 1993

Related U.S. Application Data

[63] Continuation-in-part of Ser. No. 544,218, Jun. 27, 1990, abandoned.

[51] Int. Cl.$^6$ .............................. C12Q 1/68; C07H 21/04
[52] U.S. Cl. ............................ 435/6; 435/91.2; 536/24.3; 935/77; 935/78
[58] Field of Search .................................. 435/6, 91, 91.2; 536/24.3; 935/77, 78

[56] References Cited

U.S. PATENT DOCUMENTS

| | | | |
|---|---|---|---|
| 4,582,788 | 4/1986 | Erlich | 435/6 |
| 4,683,195 | 7/1987 | Mullis et al. | 435/6 |
| 4,683,202 | 7/1987 | Mullis | 435/91.2 |

OTHER PUBLICATIONS

Bidwell, J., *Immunology Today*, 9:18–23, 1988.
Angelini et al., *Proc. Natl. Acad. Sci. USA*, 83:4489–4493, 1986.
Saiki et al., *Nature*, 324:163–166, 1986.
Bugawan et al., *J. Immunol.*, 141:4024–4030, 1988.
Gyllensten et al., *Proc. Natl. Acad. Sci. USA*, 85:7652–7656, 1988.
Fernandez et al., *Hum. Immunol.*, 28:51, 1990.
Molkentin et al., *Hum. Immunol.*, 31:114, 1991.
So et al, J. Immunology, v. 139, Nov. 15, 1987, pp. 3506–3511.
Wu et al, Proc. Natl. Acad. Sci. USA, v. 86, Apr. 1989, pp. 2757–2760.

*Primary Examiner*—John L. LeGuyader
*Attorney, Agent, or Firm*—Foley & Lardner

[57]       ABSTRACT

The invention provides an improved method for typing specific HLA sequences and other genetic sequences exhibiting similar polymorphism may be detected by sequence specific amplification (SSA). In essence, the primers used to carry out the amplification are chosen to represent sequences that distinguish one allele from another. As a result, the allele is detected if amplification occurs, and is absent if no amplification occurs. This technique can eliminate the need to conduct sequence-specific probe hybridization in order to distinguish among closely similar alleles, and can, in particular, allow resolution of complementary pairs of naturally-occurring HLA alleles which have the same polymorphisms but located on different individual alleles of each pair.

11 Claims, No Drawings

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:1:

ATTTCTTCAA TGGGACGGAG C    21

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:2:

CGCCGCTGCA CTGTGAAGCT CTC    23

( 2 ) INFORMATION FOR SEQ ID NO:3:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:3:

GTACTCTACG GGTGAGTGTT                    20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

TGTGCTACTT CACCAACGGG                    20

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

CCTTCTGGCT GTTCCAGTAC                    20

( 2 ) INFORMATION FOR SEQ ID NO:6:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

GGACGGAGCG CGTGCGTTAT                    20

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( D ) TOPOLOGY: linear ( x i ) SEQUENCE DESCRIPTION: SEQ ID NO:7:

Thr  Glu  Arg  Val  Arg  Tyr
  1                  5

( 2 ) INFORMATION FOR SEQ ID NO:8:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

CGCAGGAGCT CC                            12

( 2 ) INFORMATION FOR SEQ ID NO:9:

( i ) SEQUENCE CHARACTERISTICS:

(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:9:

CGCACGAACT CC 12

(2) INFORMATION FOR SEQ ID NO:10:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:10:

CTCGGCGCTA GG 12

(2) INFORMATION FOR SEQ ID NO:11:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:11:

TCTGGCTGTT CC 12

(2) INFORMATION FOR SEQ ID NO:12:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:12:

CCTGTCTTCC AGGATG 16

(2) INFORMATION FOR SEQ ID NO:13:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:13:

CTGTCTTCCA GGAAG 15

(2) INFORMATION FOR SEQ ID NO:14:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:14:

CGCGGCCCGC CTGT 14

(2) INFORMATION FOR SEQ ID NO:15:

(i) SEQUENCE CHARACTERISTICS:
(A) LENGTH: 12 base pairs
(B) TYPE: nucleic acid (C) STRANDEDNESS: single
(D) TOPOLOGY: linear (xi) SEQUENCE DESCRIPTION: SEQ ID NO:15:

CAGGGCCCGC CT  12

(2) INFORMATION FOR SEQ ID NO:16:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:16:

CTCTCACCAA CC  12

(2) INFORMATION FOR SEQ ID NO:17:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:17:

CTCTCCACAA CC  12

(2) INFORMATION FOR SEQ ID NO:18:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:18:

GGCCGCCCCT GC  12

(2) INFORMATION FOR SEQ ID NO:19:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:19:

CGGAACTCCC CC  12

(2) INFORMATION FOR SEQ ID NO:20:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:20:

AGGCGGCCCC AG  12

(2) INFORMATION FOR SEQ ID NO:21:

(i) SEQUENCE CHARACTERISTICS:
(A) LENGTH: 12 base pairs
(B) TYPE: nucleic acid
(C) STRANDEDNESS: single
(D) TOPOLOGY: linear ( x i ) SEQUENCE DESCRIPTION: SEQ ID NO:21:

GCGTCAAGCC GC                                                                                  1 2

( 2 ) INFORMATION FOR SEQ ID NO:22:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:22:

CGGTACACCT CC                                                                                  1 2

( 2 ) INFORMATION FOR SEQ ID NO:23:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:23:

GGCGGCAGGC GG                                                                                  1 2

( 2 ) INFORMATION FOR SEQ ID NO:24:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:24:

CGGCGTCAGG CG                                                                                  1 2

( 2 ) INFORMATION FOR SEQ ID NO:25:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:25:

CCCCGCACGA GC                                                                                  1 2

( 2 ) INFORMATION FOR SEQ ID NO:26:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:26:

CGATACACCC CC                                                                                  1 2

( 2 ) INFORMATION FOR SEQ ID NO:27:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:27:

CAGGTACATC AGATCCATCA GG    22

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

CAGGTGGGAA TTCTGGGCAG GG    22

( 2 ) INFORMATION FOR SEQ ID NO:29:

( i ) SEQUENCE CHARACTERISTICS:
        ( A ) LENGTH: 269 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 3..269

( x i ) SEQUENCE DESCRIPTION: SEQ ID NO:29:

```
CA CGT TTC TTG GAG CAG BNT AAG TCT GAG TGT CAT TTC TTC AAT GGG         47
   Arg Phe Leu Glu Gln Xaa Lys Ser Glu Cys His Phe Phe Asn Gly
    1               5                  10                  15

ACG GAG CGG GTG CGG TTC CTG GAC AGA TAC TTC CAT AAC CAG GAG GAG        95
Thr Glu Arg Val Arg Phe Leu Asp Arg Tyr Phe His Asn Gln Glu Glu
                 20                  25                  30

TAC GTG CGC TTC GAC AGC GAC GTG GGG GAG TAC CGG GCG GTG ACG GAG        143
Tyr Val Arg Phe Asp Ser Asp Val Gly Glu Tyr Arg Ala Val Thr Glu
             35                  40                  45

CTG GGG CGG CCT GAT GCC GAG TAC TGG AAC AGC CAG AAG GAC CTC CTG        191
Leu Gly Arg Pro Asp Ala Glu Tyr Trp Asn Ser Gln Lys Asp Leu Leu
         50                  55                  60

GAG CAG AAG CGG GCC GNG GTG GAC ACC TAC TGC AGA CAC AAC TAC GGG        239
Glu Gln Lys Arg Ala Xaa Val Asp Thr Tyr Cys Arg His Asn Tyr Gly
     65                  70                  75

GTT GTG GAG AGC TTC ACA GTG CAG CGG CGA                                269
Val Val Glu Ser Phe Thr Val Gln Arg Arg
 80                  85
```

( 2 ) INFORMATION FOR SEQ ID NO:30:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Arg Phe Leu Glu Gln Xaa Lys Ser Glu Cys His Phe Phe Asn Gly Thr
 1               5                  10                  15

Glu Arg Val Arg Phe Leu Asp Arg Tyr Phe His Asn Gln Glu Glu Tyr
             20                  25                  30

Val Arg Phe Asp Ser Asp Val Gly Glu Tyr Arg Ala Val Thr Glu Leu
         35                  40                  45

Gly Arg Pro Asp Ala Glu Tyr Trp Asn Ser Gln Lys Asp Leu Leu Glu
     50                  55                  60

Gln Lys Arg Ala Xaa Val Asp Thr Tyr Cys Arg His Asn Tyr Gly Val
```

Val Glu Ser Phe Thr Val Gln Arg Arg
 65                  70                  75                  80
                        85

( 2 ) INFORMATION FOR SEQ ID NO:31:

( i ) SEQUENCE CHARACTERISTICS:
      ( A ) LENGTH: 269 base pairs
      ( B ) TYPE: nucleic acid
      ( C ) STRANDEDNESS: single
      ( D ) TOPOLOGY: linear ( i x ) FEATURE:
      ( A ) NAME/KEY: unsure
      ( B ) LOCATION: 246..269

( x i ) SEQUENCE DESCRIPTION: SEQ ID NO:31:

| CACGTTTCTT | GGAGTACTCT | ACGGGTGAGT | GTTATTTCTT | CAATGGGACG | GAGCGGGTGC | 60 |
| GGTTCCTGGA | CAGATACTTC | TATAACCAAG | AGGAGTACGT | GCGCTTCGAC | AGCGACGTGG | 120 |
| GGGAGTACCG | GGCGGTGACG | GAGCTGGGGC | GGCCTAGCGC | CGAGTACTGG | AACAGCCAGA | 180 |
| AGGACTTCCT | GGAAGACAGG | CGGGCCCTGG | TGGACACCTA | CTGCAGACAC | AACTACGGGG | 240 |
| TTGGTNNNNN | NNNNNNNNNN | NNNNNNNNN | | | | 269 |

( 2 ) INFORMATION FOR SEQ ID NO:32:

( i ) SEQUENCE CHARACTERISTICS:
      ( A ) LENGTH: 269 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:32:

| CACGTTTCTT | GGAGTACTCT | ACGGGTGAGT | GTTATTTCTT | CAATGGGACG | GAGCGGGTGC | 60 |
| GGTTCCTGGA | CAGATACTTC | TATAACCAAG | AGGAGTACGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACTTCCT | GGAAGACAGG | CGGGCCCTGG | TGGACACCTA | CTGCAGACAC | AACTACGGGG | 240 |
| TTGGTGAGAG | CTTCACGGTG | CAGCGGCGA | | | | 269 |

( 2 ) INFORMATION FOR SEQ ID NO:33:

( i ) SEQUENCE CHARACTERISTICS:
      ( A ) LENGTH: 269 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:33:

| CACGTTTCTT | GGAGTACTCT | ACGGGTGAGT | GTTATTTCTT | CAATGGGACG | GAGCGGGTGC | 60 |
| GGTTCCTGGA | CAGATACTTC | TATAACCAAG | AGGAGTACGT | GCGCTTCGAC | AGCGACGTGG | 120 |
| GGGAGTACCG | GGCGGTGACG | GAGCTGGGGC | GGCCTGATGC | CGAGTACTGG | AACAGCCAGA | 180 |
| AGGACTTCCT | GGAAGACAGG | CGGGCCCTGG | TGGACACCTA | CTGCAGACAC | AACTACGGGG | 240 |
| TTGGTGAGAG | CTTCACAGTG | CAGCGGCGA | | | | 269 |

( 2 ) INFORMATION FOR SEQ ID NO:34:

( i ) SEQUENCE CHARACTERISTICS:
      ( A ) LENGTH: 269 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:34:

| | | | | | |
|---|---|---|---|---|---|
| CACGTTTCTT | GGAGTACTCT | ACGGGTGAGT | GTTATTTCTT | CAATGGGACG | GAGCGGGTGC | 60
| GGTTCCTGGA | CAGATACTTC | TATAACCAAG | AGGAATACGT | GCGCTTCGAC | AGCGACGTGG | 120
| GGGAGTACCG | GGCGGTGACG | GAGCTGGGGC | GGCCTAGCGC | CGAGTACTGG | AACAGCCAGA | 180
| AGGACATCCT | GGAAGACAGG | CGGGCCCTGG | TGGACACCTA | CTGCAGACAC | AACTACGGGG | 240
| TTGGTGAGAG | CTTCACAGTG | CAGCGGCGA  |            |            |            | 269

( 2 ) INFORMATION FOR SEQ ID NO:35:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i x ) FEATURE:
        ( A ) NAME/KEY: unsure
        ( B ) LOCATION: 246..269

( x i ) SEQUENCE DESCRIPTION: SEQ ID NO:35:

| | | | | | |
|---|---|---|---|---|---|
| CACGTTTCTT | GGAGTACTCT | ACGGGTGAGT | GTTATTTCTT | CAATGGGACG | GAGCGGGTGC | 60
| GGTTCCTGGA | CAGATACTTC | TATAACCAAG | AGGAGTACGT | GCGCTTCGAC | AGCGACGTGG | 120
| GGGAGTACCG | GGCGGTGACG | GAGCTGGGGC | GGCCTAGCGC | CGAGTACTGG | AACAGCCAGA | 180
| AGGACATCCT | GGAAGACAGG | CGGGCCCTGG | TGGACACCTA | CTGCAGACAC | AACTACGGGG | 240
| TTGGTNNNNN | NNNNNNNNNN | NNNNNNNNN  |            |            |            | 269

( 2 ) INFORMATION FOR SEQ ID NO:36:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

| | | | | | |
|---|---|---|---|---|---|
| CACGTTTCTT | GGAGTACTCT | ACGGGTGAGT | GTTATTTCTT | CAATGGGACG | GAGCGGGTGC | 60
| GGTTCCTGGA | CAGATACTTC | TATAACCAAG | AGGAGTACGT | GCGCTTCGAC | AGCGACGTGG | 120
| GGGAGTACCG | GGCGGTGACG | GAGCTGGGGC | GGCCTGATGC | CGAGTACTGG | AACAGCCAGA | 180
| AGGACTTCCT | GGAAGACAGG | CGGGCCCTGG | TGGACACCTA | CTGCAGACAC | AACTACGGGG | 240
| TTGTGGAGAG | CTTCACAGTG | CAGCGGCGA  |            |            |            | 269

( 2 ) INFORMATION FOR SEQ ID NO:37:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

| | | | | | |
|---|---|---|---|---|---|
| CACGTTTCTT | GGAGTACTCT | ACGGGTGAGT | GTTATTTCTT | CAATGGGACG | GAGCGGGTGC | 60
| GGTTCCTGGA | CAGATACTTC | TATAACCAAG | AGGAGTACGT | GCGCTTCGAC | AGCGACGTGG | 120
| GGGAGTACCG | GGCGGTGACG | GAGCTGGGGC | GGCCTAGCGC | CGAGTACTGG | AACAGCCAGA | 180
| AGGACTTCCT | GGAAGACAGG | CGGGCCGCGG | TGGACACCTA | CTGCAGACAC | AACTACGGGG | 240
| TTGGTGAGAG | CTTCACAGTG | CAGCGGCGA  |            |            |            | 269

( 2 ) INFORMATION FOR SEQ ID NO:38:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

| | | | | | |
|---|---|---|---|---|---|
| CACGTTTCTT | GGAGTACTCT | ACGGGTGAGT | GTTATTTCTT | CAATGGGACG | GAGCGGGTGC | 60 |
| GGTTACTGGA | GAGACACTTC | CATAACCAGG | AGGAGCTCCT | GCGCTTCGAC | AGCGACGTGG | 120 |
| GGGAGTTCCG | GGCGGTGACG | GAGCTGGGGC | GGCCTGTCGC | CGAGTCCTGG | AACAGCCAGA | 180 |
| AGGACATCCT | GGAAGACAGG | CGCGCCGCGG | TGGACACCTA | TTGCAGACAC | AACTACGGGG | 240 |
| CTGTGGAGAG | CTTCACAGTG | CAGCGGCGA | | | | 269 |

( 2 ) INFORMATION FOR SEQ ID NO:39:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

| | | | | | |
|---|---|---|---|---|---|
| CACGTTTCTT | GGAGTACTCT | ACGGGTGAGT | GTTATTTCTT | CAATGGGACG | GAGCGGGTGC | 60 |
| GGTTACTGGA | GAGACACTTC | CATAACCAGG | AGGAGCTCCT | GCGCTTCGAC | AGCGACGTGG | 120 |
| GGGAGTTCCG | GGCGGTGACG | GAGCTGGGGC | GGCCTGTCGC | CGAGTCCTGG | AACAGCCAGA | 180 |
| AGGACTTCCT | GGAAGACAGG | CGCGCCGCGG | TGGACACCTA | TTGCAGACAC | AACTACGGGG | 240 |
| CTGTGGAGAG | CTTCACAGTG | CAGCGGCGA | | | | 269 |

( 2 ) INFORMATION FOR SEQ ID NO:40:

( i ) SEQUENCE CHARACTERISTICS:
        ( A ) LENGTH: 282 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..282

( x i ) SEQUENCE DESCRIPTION: SEQ ID NO:40:

| | | | | | | | | | | | | | | | | |
|---|---|---|---|---|---|---|---|---|---|---|---|---|---|---|---|---|
| AGA | GAC | TCT | CCC | GAG | GAT | TTC | GTG | TAC | CAG | TTT | AAG | GGC | ATG | TGC | TAC | 48 |
| Arg | Asp | Ser | Pro | Glu | Asp | Phe | Val | Tyr | Gln | Phe | Lys | Gly | Met | Cys | Tyr | |
| 1 | | | | 5 | | | | | 10 | | | | | 15 | | |
| TTC | ACC | AAC | GGG | ACG | GAG | CGC | GTG | CGT | CTT | GTG | ACC | AGA | TAC | ATC | TAT | 96 |
| Phe | Thr | Asn | Gly | Thr | Glu | Arg | Val | Arg | Leu | Val | Thr | Arg | Tyr | Ile | Tyr | |
| | | | 20 | | | | | 25 | | | | | 30 | | | |
| AAC | CGA | GAG | GAG | TAC | GCG | CGC | TTC | GAC | AGC | GAC | GTG | GGG | GTG | TAC | CGG | 144 |
| Asn | Arg | Glu | Glu | Tyr | Ala | Arg | Phe | Asp | Ser | Asp | Val | Gly | Val | Tyr | Arg | |
| | | 35 | | | | | 40 | | | | | 45 | | | | |
| GCG | GTG | ACG | CCG | CAG | GGG | CGG | CCT | GAC | GCC | GAG | TAC | TGG | AAC | AGC | CAG | 192 |
| Ala | Val | Thr | Pro | Gln | Gly | Arg | Pro | Asp | Ala | Glu | Tyr | Trp | Asn | Ser | Gln | |
| | 50 | | | | | 55 | | | | | 60 | | | | | |
| AAG | GAA | GTC | CTG | GAG | GGG | ACC | CGG | GCG | GAG | TTG | GAC | ACG | GTG | TGC | AGA | 240 |
| Lys | Glu | Val | Leu | Glu | Gly | Thr | Arg | Ala | Glu | Leu | Asp | Thr | Val | Cys | Arg | |
| 65 | | | | | 70 | | | | | 75 | | | | | 80 | |
| CAC | AAC | TAC | GAG | GTG | GAG | TTC | CGC | GGG | ACC | TTG | CAG | AGG | AGA | | | 282 |
| His | Asn | Tyr | Glu | Val | Glu | Phe | Arg | Gly | Thr | Leu | Gln | Arg | Arg | | | |
| | | | | 85 | | | | | 90 | | | | | | | |

( 2 ) INFORMATION FOR SEQ ID NO:41:

( i ) SEQUENCE CHARACTERISTICS:
        ( A ) LENGTH: 94 amino acids
        ( B ) TYPE: amino acid
        ( D ) TOPOLOGY: linear ( i i ) MOLECULE TYPE: protein ( x i ) SEQUENCE DESCRIPTION: SEQ ID NO:41:

```
Arg Asp Ser Pro Glu Asp Phe Val Tyr Gln Phe Lys Gly Met Cys Tyr
 1               5                  10                  15

Phe Thr Asn Gly Thr Glu Arg Val Arg Leu Val Thr Arg Tyr Ile Tyr
            20                  25                  30

Asn Arg Glu Glu Tyr Ala Arg Phe Asp Ser Asp Val Gly Val Tyr Arg
        35                  40                  45

Ala Val Thr Pro Gln Gly Arg Pro Asp Ala Glu Tyr Trp Asn Ser Gln
    50                  55                  60

Lys Glu Val Leu Glu Gly Thr Arg Ala Glu Leu Asp Thr Val Cys Arg
65                  70                  75                  80

His Asn Tyr Glu Val Glu Phe Arg Gly Thr Leu Gln Arg Arg
                85                  90
```

( 2 ) INFORMATION FOR SEQ ID NO:42:

( i ) SEQUENCE CHARACTERISTICS:
        ( A ) LENGTH: 282 base pairs
        ( B ) TYPE: nucleic acid
        ( C ) STRANDEDNESS: single
        ( D ) TOPOLOGY: linear ( i x ) FEATURE:
        ( A ) NAME/KEY: unsure
        ( B ) LOCATION: 1..13

( x i ) SEQUENCE DESCRIPTION: SEQ ID NO:42:

```
NNNNNNNNN   NNNAGGATTT   CGTGTACCAG   TTTAAGGCCA   TGTGCTACTT   CACCAACGGG        60

ACGGAGCGCG   TGCGTTATGT   GACCAGATAC   ATCTATAACC   GAGAGGAGTA   CGCACGCTTC       120

GACAGCGACG   TGGAGGTGTA   CCGGGCGGTG   ACGCCGCTGG   GGCCGCCTGA   CGCCGAGTAC       180

TGGAACAGCC   AGAAGGAAGT   CCTGGAGAGG   ACCCGGGCGG   AGTTGGACAC   GGTGTGCAGA       240

CACAACTACC   AGTTGGAGCT   CCGCACGACC   TTGCAGCGGC   GA                           282
```

( 2 ) INFORMATION FOR SEQ ID NO:43:

( i ) SEQUENCE CHARACTERISTICS:
        ( A ) LENGTH: 282 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

```
AGAGACTCTC   CCGAGGATTT   CGTGTACCAG   TTTAAGGGCA   TGTGCTACTT   CACCAACGGG        60

ACGGAGCGCG   TGCGTCTTGT   GACCAGATAC   ATCTATAACC   GAGAGGAGTA   CGCACGCTTC       120

GACAGCGACG   TGGGGGTGTA   TCGGGCGGTG   ACGCCGCTGG   GGCCGCCTGC   CGCCGAGTAC       180

TGGAACAGCC   AGAAGGAAGT   CCTGGAGAGG   ACCCGGGCGG   AGTTGGACAC   GGTGTGCAGA       240

CACAACTACC   AGTTGGAGCT   CCGCACGACC   TTGCAGCGGC   GA                           282
```

( 2 ) INFORMATION FOR SEQ ID NO:44:

(i) SEQUENCE CHARACTERISTICS:
   (A) LENGTH: 282 base pairs
   (B) TYPE: nucleic acid
   (C) STRANDEDNESS: single
   (D) TOPOLOGY: linear (xi) SEQUENCE DESCRIPTION: SEQ ID NO:44:

| | | | | | | |
|---|---|---|---|---|---|---|
| AGAGACTCTC | CCGAGGATTT | CGTGTACCAG | TTTAAGGGCA | TGTGCTACTT | CACCAACGGG | 60 |
| ACCGAGCGCG | TGCGTCTTGT | GACCAGATAC | ATCTATAACC | GAGAGGAGTA | CGCACGCTTC | 120 |
| GACAGCGACG | TGGGGGTGTA | TCGGGCGGTG | ACGCCGCTGG | GGCCGCCTGA | CGCCGAGTAC | 180 |
| TGGAACAGCC | AGAAGGAAGT | CCTGGAGAGG | ACCCGGGCGG | AGTTGGACAC | GGTGTGCAGA | 240 |
| CACAACTACC | AGTTGGAGCT | CCGCACGACC | TTGCAGCGGC | GA | | 282 |

(2) INFORMATION FOR SEQ ID NO:45:

(i) SEQUENCE CHARACTERISTICS:
   (A) LENGTH: 282 base pairs
   (B) TYPE: nucleic acid
   (C) STRANDEDNESS: single
   (D) TOPOLOGY: linear (xi) SEQUENCE DESCRIPTION: SEQ ID NO:45:

| | | | | | | |
|---|---|---|---|---|---|---|
| AGAGACTCTC | CCGAGGATTT | CGTGTACCAG | TTTAAGGGCA | TGTGCTACTT | CACCAACGGG | 60 |
| ACGGAGCGCG | TGCGTCTTGT | GACCAGATAC | ATCTATAACC | GAGAGGAGTA | CGCACGCTTC | 120 |
| GACAGCGACG | TGGGGGTGTA | TCGGGCGGTG | ACGCCGCTGG | GGCCGCCTGA | CGCCGAGTAC | 180 |
| TGGAACAGCC | AGAAGGAAGT | CCTGGAGAGG | ACCCGGGCGG | AGTTGGACAC | GGTGTGCAGA | 240 |
| CACAACTACC | AGTTGGAGCT | CCGCACGACC | TTGCAGCGGC | GA | | 282 |

(2) INFORMATION FOR SEQ ID NO:46:

(i) SEQUENCE CHARACTERISTICS:
   (A) LENGTH: 282 base pairs
   (B) TYPE: nucleic acid
   (C) STRANDEDNESS: single
   (D) TOPOLOGY: linear (xi) SEQUENCE DESCRIPTION: SEQ ID NO:46:

| | | | | | | |
|---|---|---|---|---|---|---|
| AGAGACTCTC | CCGAGGATTT | CGTGTACCAG | TTTAAGGCCA | TGTGCTACTT | CACCAACGGG | 60 |
| ACGGAGCGCG | TGCGTTATGT | GACCAGATAC | ATCTATAACC | GAGAGGAGTA | CGCACGCTTC | 120 |
| GACAGCGACG | TGGAGGTGTA | CCGGGCGGTG | ACGCCGCTGG | GGCCGCCTGC | CGCCGAGTAC | 180 |
| TGGAACAGCC | AGAAGGAAGT | CCTGGAGAGG | ACCCGGGCGG | AGTTGGACAC | GGTGTGCAGA | 240 |
| CACAACTACC | AGTTGGAGCT | CCGCACGACC | TTGCAGCGGC | GA | | 282 |

METHOD FOR HLA TYPING

This application is a continuation-in-part of U.S. Ser. No. 07/544,218, filed Jun. 27, 1990, now abandoned.

Field of the Invention

The invention relates to a method of typing human leukocyte antigens for purposes of, for example, tissue matching, identification or disease susceptibility. In particular, this invention relates to HLA-DRB1 and HLA-DQB1 typing, and methods and probes useful for such typing.

BACKGROUND OF THE INVENTION

The major histocompatibility complex of humans is a cluster of genes occupying a region located on the sixth chromosome. Human leukocyte antigen ("HLA") genes are highly polymorphic and code for human leukocyte antigens whose structural variation is a major factor in influencing tissue transplantation, immunity and autoimmunity. The polymorphic HLA proteins have been designated HLA-A, -B, -C, -DR, -DQ and -DP. The HLA-A, -B, and -C proteins are described as Class I HLA proteins and are characterized by a polymorphic chain, alpha, and a nonpolymorphic chain, beta 2 microglobulin. The HLA-DR, -DQ and -DP proteins are classified as Class II HLA proteins and are comprised of two polypeptide chains, an alpha chain and a highly polymorphic beta chain. These HLA-D-region proteins are encoded by loci designated HLA-DRA, -DRB1, -DRB3, -DRB4, -DRB5, -DQA1, -DQB1, -DPA1 and -DPB1. HLA-DRA, -DQA1 and -DPA1 are much less polymorphic than HLA-DRB1, DQB1 and -DPB1.

The proteins encoded by the polymorphic HLA loci are most commonly typed using serological methods. One of the limitations of serological typing is that it does not differentiate between many of the alleles that are known to exist in the population. This has prompted the development of methods for analysis of HLA polymorphism at the genetic level, as described in Bidwell, J., *Immunology Today* 9:18–23, 1988, and Angelini et al., *Proc. Natl. Acad. Sci. USA*, 83:4489–4493, 1986.

One such method involves the use of DNA restriction fragment length polymorphism (RFLP) as a basis for HLA typing. See Erlich, U.S. Pat. No. 4,582,788, issued Apr. 15, 1986, the contents of which are incorporated herein by reference. RFLP analysis, however, fails to differentiate between certain alleles that are known to exist in the population (e.g., subtypes of HLA-DR4), and thus, cannot be used to distinguish certain combinations of alleles known to exist in the population.

More recently, utilizing the polymerase chain reaction (PCR) process, as described in U.S. Pat. No. 4,683,202, issued Jul. 28, 1987, the contents of which are incorporated herein by reference, researchers have used sequence-specific oligonucleotide ("SSO") probe hybridization to perform HLA-Class II typing. That method entails amplifying a polymorphic region of an HLA locus using the PCR, contacting the amplified DNA to a plurality of sequence-specific oligonucleotide probes under hybridizing conditions, and detecting hybrids formed between the amplified DNA and the sequence-specific oligonucleotide probes. Alleles of HLA-DQ alpha and HLA-DP alpha and beta genes have been identified in the aforementioned manner. See Saiki et al., *Nature*, 324:163–166, 1986, Bugawan et al., *J. Immunol.*, 141:4024–4030, 1988, and Gyllensten et al., *Proc. Natl. Acad. Sci. USA*, 85:7652–7656, 1988, the contents of which are incorporated herein by reference.

Reported oligotyping strategies utilizing sequence-specific oligonucleotide probes have failed, however, to resolve many heterozygotic allelic combinations. For example, Fernandes et al., did not resolve all HLA-DRB1 alleles associated with HLA-DRw52 haplotypes due to the sharing of polymorphic sequences within this group of alleles. See Fernandez et al., *Hum Immunol* 28:51, 1990, the contents of which are incorporated herein by reference. Similarly, Molkentin et al. failed to fully resolve HLA-DQB1-03 alleles using sequence-specific oligonucleotide probe hybridization. Molkentin et al., *Hum. Immunol.*, 31:114, 1991, the contents of which are incorporated herein by reference.

The present invention addresses some of the shortcomings of known HLA typing methods and provides an improved process for resolving HLA alleles and for resolving heterozygotic allelic combinations.

SUMMARY OF THE INVENTION

The present invention provides an improved method for typing specific HLA sequences and other genetic sequences exhibiting similar polymorphism may be detected by sequence specific amplification (SSA). In essence, the primers used to carry out the amplification are chosen to represent sequences that distinguish one allele from another. As a result, the allele is detected if amplification occurs, and is absent if no amplification occurs. This technique can eliminate the need to conduct sequence-specific hybridization in order to distinguish among closely similar alleles.

One method for HLA typing according to the invention includes the steps of amplifying an HLA DNA sequence of a subject using a pair of primers selected to amplify a specific predetermined sequence associated with a preselected one of a plurality of known basic HLA allele types, each of which basic types comprises a number of different alleles, under sufficiently stringent conditions to selectively amplify DNA of the one basic type, and analyzing the amplified DNA to detect which one of the specific alleles associated with the basic type is present in the DNA of the subject. The analyzing step may be carried out in a variety of ways, such as by additional sequence-specific amplifications or oligonucleotide probe hybridizations, and may be conducted before or after the sequence-specific amplification step. The analyzing step preferably further includes the steps of:

(a) bringing a labelled oligonucleotide probe that recognizes an allelic polymorphism at the HLA locus of the basic type into contact with a sample of the amplified HLA sequence under hybridizing conditions;

(b) detecting the formation of a DNA duplex by the labelled probe and the amplified HLA sequence;

(c) repeating steps (a) and (b) with different labelled probes and additional samples of the amplified HLA sequence as needed to identify differences between the amplified HLA sequence and a corresponding HLA consensus sequence; and (d) correlating the results with known alleles of the basic HLA type to determine which allele or alleles are present in the subject.

In accordance with this embodiment of the invention, the first step determines whether the HLA type of the amplified DNA falls into one or more basic types, which basic types include several subtypes, i.e., specific alleles. For example, the HLA-DRB1*08 basic type includes HLA-DRB1*0801, HLA-DRB1*08021, HLA-DRB1*08022, HLA-DRB1*08031, HLA-DRB1*08032, HLA-DRB1*0804, and HLA-DRB1*0805. These alleles, along with HLA-DRB1*1201, HLA-DRB1*1202 and HLA-DRB1*1404, share a unique sequence at positions 10–16 that differs from other known basic HLA-DRB types. The first level of typing could, therefore, be carried out using an oligonucleotide probe designed to detect this polymorphism, rather than by sequence-specific amplification. In either case, the two-stage analysis is particularly useful and effective for so called "patchwork alleles" wherein newly discovered alleles often represent new combinations of known polymorphisms at different sites. HLA-DR beta alleles, of which more than about 70 are now known, include many such patchwork alleles that are particularly difficult to resolve.

In one embodiment of this method, the invention provides an improved method for HLA typing HLA-DRB1*08 and *12 and HLA-DQB1*03 alleles. The method involves selectively amplifying the HLA-DRB1*08 and *12 alleles, or DQB1*03 alleles, and detecting polymorphic sequences by sequence-specific oligonucleotide probe hybridization.

The HLA typing methods according to the invention are useful as part of a method for tissue matching for transplantation. The information obtained from the typing can also be used for identification (forensic or paternity testing) and disease susceptibility such as for purposes of preventative therapy or insurance. For example, a potential bone marrow recipient and a pool of potential donors are HLA typed using standard serological and/or oligotyping procedures. If the recipient and any of the potential donors test positive for HLA-DRB1-08 or 12 oligotypes, or certain DQB1-03 heterozygote combinations, HLA samples from the recipient and potential donors who test positive are further analyzed and the HLA-DRB1-08 and 12 oligotypes and certain DQB1-03 oligotypes are further resolved according to the method of the invention.

More specifically, the present invention is directed to a method for typing HLA-DRB1*08 and *12 alleles, comprising the steps of:

(a) amplifying an HLA-DR beta sequence using primers, one of which will hybridize with a nucleotide sequence corresponding to a nucleotide sequence occupying amino acid positions 10 to 16 of the HLA-DRB1*08 and *12 alleles, and the other of said primers which will hybridize with a nucleotide sequence corresponding to an HLA-DR beta consensus sequence, to obtain an amplified HLA-DR beta sequence;

(b) bringing a plurality of labeled oligonucleotide probes into contact with a sample of the amplified HLA-DR beta sequence under hybridizing conditions, wherein each of said plurality of probes recognizes a different allelic polymorphism between amino acid positions corresponding to said primers; and (c) detecting the formation of a DNA hybrid between any of said plurality of labeled oligonucleotide probes and said amplified HLA-DR beta sequence.

The invention also entails a method for typing HLA-DQB1*03 alleles, which comprises the steps of:

(a) amplifying an HLA-DQ beta sequence of DNA of a human subject using primers, one of which will hybridize with a nucleotide sequence corresponding to an amino acid sequence positions 21 to 26 of the HLA-DQB1*03 allele, and the other of said primers which will hybridize with a nucleotide sequence corresponding to an HLA-DQ beta consensus sequence, to obtain an amplified HLA-DQ beta sequence;

(b) bringing a plurality of labeled oligonucleotide probes into contact with a sample of the amplified HLA-DQ beta sequence under hybridizing conditions, wherein each of said plurality of probes recognizes a different allelic polymorphism between amino acid positions corresponding to said primers; and (c) detecting the formation of a DNA duplex between any of said plurality of labeled oligonucleotide probes and said amplified HLA-DQ beta sequence.

The inventors have also discovered two new HLA alleles, now designated HLA-DRB1*0805 and HLA-DQB1*0304. Accordingly, the invention further provides a method for typing for these new alleles, either by the improved method of the invention described above, or by other known methods, such as locus-specific amplification followed by oligonucleotide probe hybridization.

The invention further addresses resolving particularly difficult combinations of alleles wherein two pairs of alleles are known to exist in the population, each pair complementing the other as explained hereafter. In such a method of HLA typing including the steps of determining the HLA type of a tissue sample and comparing the result with known HLA types, the improvement of the invention involves selectively amplifying one of a first pair of alleles of the same known basic HLA allele type, both of which pair are present in the sample, in order to distinguish the first pair from a second pair of alleles not present in the sample which contains the same HLA polymorphisms as the first pair within the amplified sequence, but some of which polymorphisms are located on different individual alleles compared to the first pair so that the second pair of alleles is different from the first pair. In the example described below, the first and second pairs are DQB1*0304/DQB1*0303 and DQB1*0301/DQB1*0302, but the method is applicable whenever this type of situation arises, in HLA or other comparable forms of genetic typing.

These and other aspects of the invention, such as the specific primers and probes used in the examples, are described further in the description which follows.

DETAILED DESCRIPTION

HLA typing according to the invention may be conducted in two or more stages. In an initial stage, subject DNA from highly conserved regions is amplified and then hybridized with labelled probes to identify basic type, that is, groups usually organized according to association with a single serologically defined specificity, such as DRB1*01 to DRB1*12, formerly called DR1,2,3,4,5,w6,7,w8,9,w10, w12,w52,w53, or the various HLA-DQB1 types. The purpose of the first stage of testing is to establish the number of alleles present in each sample under conditions which substantially reduce the likelihood of false negative results due to failed amplification. Use of primers encoding fairly well conserved regions of a locus will increase the likelihood that unknown alleles will be amplified and potentially detected by hybridization with oligonucleotide probes. Furthermore, failure to produce an amplified product will indicate a failure of the assay.

In the second stage, the group or basic type identified in the first stage determines which of a set of allele-specific primers will be used for sequence-specific amplification (SSA). The first of two primers for second stage amplification comprises a sequence common to each allele of the group identified in stage one, but different from other groups identified in stage one, optionally attached to a molecule such as biotin useful in subsequent selection. The second primer may be a mixture of different labelled primers, complementary to two or more sequences within the group, but SSA may simply be performed with just one second primer to detect the presence of a single group of alleles, such as the nine alleles of HLA-DRB1*08 and *12.

In a third stage, the specific allele is determined. This can be done at the same time as the second stage by amplification using a primer mixture, as mentioned above, or as an additional step by use of conventional radiolabelled hybridization probes that hybridize to the sites at which the alleles differ. Various other combinations of oligotyping and SSA may be used to determine which allele is present. For example, locus-specific amplification may be carried out, followed by analysis with oligonucleotide probes that limit the unknown alleles in the sample to one of several possibilities. SSA may then be performed to further limit the possibilities to the needed level of specificity, and may be sufficient to type a specific allele.

As described in detail below, sequence-specific hybridization of oligonucleotide probes to products of a locus-specific amplification is incapable of resolving certain combinations of alleles. This problem can be resolved by sequence-specific amplification. New alleles comprising different combinations of known polymorphic residues can be defined, and new alleles lacking a previously defined sequence can be detected by the lack of amplification or hybridization at one or more positions.

As examples of the foregoing method, the present invention encompasses Selective intralocus DNA amplification of HLA-DRB1*08 and *12 and HLA-DQB1*03 alleles in conjunction with sequence-specific oligonucleotide probe hybridization to identify the specific alleles which are selectively amplified. DR and DQ type information is useful for HLA matching of HLA-DRB1-08 and -12 oligotypes and HLA-DQB1-03 oligotypes, especially for purposes of tissue transplantation, e.g., in the selection of donors for bone marrow transplantation. One important advantage provided by the method of the present invention is its better resolution than reported sequence-specific oligonucleotide probe hybridization typing strategies of HLA-DRB1*08 and *12 alleles and HLA-DQB1*03 alleles.

Table 1 sets forth nucleotide sequences for HLA-DR*08 and *12 alleles at locus B1, and Table 2 sets forth nucleotide sequences for HLA-DQB1*03 alleles. The consensus sequence is set forth along the top of each table. The various alleles have the same sequence as the consensus sequence at all positions noted with a dash (-), and differ from the consensus sequence where a nucleotide (A,G,C or T) is given or where an amino acid is given using the single letter code. Serological and cellular specificities assigned to the cell from which sequences were derived are indicated. The nomenclature corresponds to the World Health Committee for Factors of the HLA, as reported in Bodmer et al., *Tissue Antigens,* 39:161–173 (1992) the text of which is incorporated herein by reference.

TABLE 1

```
                                              6    R   F   L   E   Q   X   K   S   E   C   H   F   F   N   G   T   E   R   V
                                                 CACGTTTCTTGGAGCAGxxTAAGTCTGAGTGTCATTTCTTCAATGGGACGGAGCGGGTGC
DR cons              (SEQ ID NO:30)
DRB1*0801-2,4-5      (SEQ ID NO:29)           (SEQ ID NOS:31,32,33,36 AND 37)   ----T-CTC---C--GG-------T------------
DRB1*08031           (SEQ ID NO:34)                                             ----T-CTC---C--GG-------T------------
DRB1*08032           (SEQ ID NO:35)                                             ----T-CTC---C--GG-------T------------
DRB1*1201,2          (SEQ ID NOS:38 AND 39)                                     ----T-CTC---C--GG-------T------------
DR cons              (SEQ ID NO:29)           CACGTTTCTTGGAGCAGxxTAAGTCTGAGTGTCATTTCTTCAATGGGACGGAGCGGGTGC
                                                       10            20           30           40           50           60

R   F   L   D   R   Y   F   H   N   Q   E   E   Y   V   R   F   D   S   D   V   G   E   Y   R   A
                                                GGTTCCTGGACAGATACTTCCATAACCAGGAGGAGTACGTGCGCTTCGACAGCGACGTGGGGGAGTACCGGGCG
DR cons              (SEQ ID NO:30)
DRB1*0801-2,4-5                                  ------------T-----------A---------------------------------------
DRB1*08031                                       ------------T-----------A---------------------------------------
DRB1*08032                                       ------------T-----------A---------------------------------------
DRB1*1201,2                                      ----A------G--C-----------------CT-C--------------T--------------
                                                       70           80           90           100          110          120          130

50   V   T   E   L   G   R   P   D   A   E   Y   W   N   S   Q   K   D   L   L   E   Q
                                                GTGACGGAGCTGGGGCGGCCTGATGCCGAGTACTGGAACAGCCAGAAGGACCTCCTGGAGCAGA
DR cons              (SEQ ID NO:30)
DRB1*0801            (SEQ ID NO:31)              ---------------------------AGC-----------------T-------AG--C---
DRB1*08021           (SEQ ID NO:32)              ---------------------------AGC-----------------T-------AG--C---
DRB1*08022           (SEQ ID NO:33)              ---------------------------AGC-----------------T-------AG--C---
DRB1*08031           (SEQ ID NO:34)              ---------------------------AGC----------------A--------AG--C---
DRB1*08032           (SEQ ID NO:35)              ---------------------------AGC----------------A--------AG--C---
DRB1*0804            (SEQ ID NO:36)              ---------------------------AGC-----------------T-------AG--C---
DRB1*0805            (SEQ ID NO:37)              ---------------------------AGC-----------------T-------AG--C---
DRB1*1201            (SEQ ID NO:38)              ----------------------------TC----C-----------A--------AG--C---
DRB1*1202            (SEQ ID NO:39)              ----------------------------TC----C-----------T--------AG--C---
DR cons              (SEQ ID NO:29)             GTGACGGAGCTGGGGCGGCCTGATGCCGAGTACTGGAACAGCCAGAAGGACCTCCTGGAGCAGA
                                                      140          150          160          170          180          190
```

TABLE 1-continued

```
                         80                          90
          K R A X V D T Y C R H N Y G V V E S F T V Q R R
DR cons   AGCGGGGCCGxGGTGGACACCTACTGCAGACACAACTACGGGGTTGTGGAGAGCTTCACAGTGCAGCGGCGA
DRB1*0801 G---------CT-----------------------------------GT--------------------
DRB1*08021 G---------CT------------------------------------G--------------------
DRB1*08022 G---------CT-------------------CT---------------G--------------------
DRB1*08031 G---------CT-------------------CT--------------GT--------------------
DRB1*08032 G---------CT------------------------------------GT--------------------
DRB1*0804 G---------CT------------------------------------GT--------------------
DRB1*0805 G---------GC------------------------------------GT--------------------
DRB1*1201 G---C-----C---------T-----------------C------------------------------
DRB1*1202 G---C-----C---------T-------T---------C------------------------------
DR cons   AGCGGGGCCGxGGTGGACACCTACTGCAGACACAACTACGGGGTTGTGGAGAGCTTCACAGTGCAGCGGCGA
          200       210       220       230       240       250       260
```

TABLE 2

```
                                              10                            20
                       R  D  S  P  E  D  F  V  Y  Q  F  K  G  M  C  Y  F  T  N  G  T  E
CONSENSUS  (SEQ ID NO:41)
           (SEQ ID NO:40) AGAGACTCTCCCGAGGATTTCGTGTACCAGTTTAAGGGCATGTGCTACTTCACCAACGGGACGGAGC
DQB1*0301  (SEQ ID NO:42) ----------------------------------------------------------------
DQB1*0302  (SEQ ID NO:43) -----------------------------------------------C----------------
DQB1*03031 (SEQ ID NO:44) ----------------------------------------------------------------
DQB1*03032 (SEQ ID NO:45) ----------------------------------------------------------------
DQB1*0304  (SEQ ID NO:46) -----------------------------------------------C----------------

CONSENSUS  (SEQ ID NO:40) AGAGACTCTCCCGAGGATTTCGTGTACCAGTTTAAGGGCATGTGCTACTTCACCAACGGGAGC 30                            40
                       R  V  R  L  V  T  R  Y  I  Y  N  R  E  E  Y  A  R  F  D  S  D  V  G
CONSENSUS  (SEQ ID NO:40) GCGTGCGTCTTGTGACCAGATACATCTATAACCGAGAGGAGTACGCGCGCTTCGACAGCGACGTGGGG
DQB1*0301  (SEQ ID NO:42) ------TA--------------------------------------------------------A-
DQB1*0302  (SEQ ID NO:43) ----------------------------------------------------------------
DQB1*03031 (SEQ ID NO:44) ----------------------------------------------------------------A-
DQB1*03032 (SEQ ID NO:45) ----------------------------------------------------------------A-
DQB1*0304  (SEQ ID NO:46) ------TA--------------------------------------------------------A-

CONSENSUS  (SEQ ID NO:40) GCGTGCGTCTTGTGACCAGATACATCTATAACCGAGAGGAGTACGCGCGCTTCGACAGCGACGTGGGG 50                            60
                       V  Y  R  A  V  T  P  Q  G  R  P  D  A  E  Y  W  N  S  Q  K  E  V  L  E
CONSENSUS              GTGTACCGGGCGGTGACGCCGCAGGGGCGGCCTGACGCCGAGTACTGGAACAGCCAGAAGGAAGTCCTGGAGG
DQB1*0301              --------------------T------C----------------------------------------A
DQB1*0302              ---------T----------T------C----------------------------------------A
DQB1*03031             --------------------T------C----------------------------------------A
DQB1*03032             ---------T----------T------C----------------------------------------A
DQB1*0304              --------------------T------C----------------------------------------A

CONSENSUS              GTGTACCGGGCGGTGACGCCGCAGGGGCGGCCTGACGCCGAGTACTGGAACAGCCAGAAGGAAGTCCTGGAGG 70                            80                      90
                       G  T  R  A  E  L  D  T  V  C  R  H  N  Y  E  V  E  F  R  G  T  L  Q  R  R
CONSENSUS              GGACCCGGGCGGAGTTGGACACGGTGTGCAGACACAACTACGAGGTGGAGTTCCGCGGGACCTTGCAGAGGAGA
```

TABLE 2-continued

| | | |
|---|---|---|
| DQB1*0301 | ------------------------------ | ----C--T-----C-------AC--------------C--C--- |
| DQB1*0302 | ------------------------------ | ----C--T-----C-------AC--------------C--C--- |
| DQB1*03031 | ------------------------------ | ----C--T-----C-------AC--------------C--C--- |
| DQB1*03032 | ------------------------------ | ----C--T-----C-------AC--------------C--C--- |
| DQB1*0304 | ------------------------------ | ----C--T-----C-------AC--------------C--C--- |
| CONSENSUS | GGACCCGGCGGAGTTGGACACGGTGTGCAGACACAACTACGAGGTGGAGTTCCGGGACCTTGCAGAGAGA | |

Of the HLA-DR beta sequences given in Table 1, DRB1*0805 is a new sequence identified as part of the present invention. Of the HLA-DQ beta sequences given in Table 2, DQB1*0304 is a new sequence identified as part of the present invention.

Tables 1 and 2 illustrate that there is substantial polymorphism among the HLA-DRB1*08 and *12 alleles and DQB1*03 alleles. These alleles are closely similar, and vary by as little as a single nucleotide. Thus, the need for a typing method which can identify these single nucleotide differences is apparent.

Selective intra-locus amplification of HLA-DRB1*08 and *12 alleles and HLA-DQB1*03 alleles provides a more sensitive assay for resolving those alleles than oligotyping strategies used prior to the present invention. The HLA-DQB1*0304 allele is a patchwork allele containing a novel combination of polymorphic sequences that are characteristic of known alleles. Thus, using known oligotyping procedures, that allele could be assigned an inaccurate oligotype because the hybridization pattern of DQB1*0304 is identical to that of two known alleles. For example, if the DQB1*0304 allele is present in combination with a DQB1*0303 allele, an oligotype indicative of a DQB1*0301/DQB1*0302 heterozygote would be assigned using published oligotyping methods; see Gao, et al., *Hum. Immunol.*, 7:40, 1990 and Lanchbury, et al., *Hum. Immunol.*, 27:136, 1990.

It is also possible that the DQB1*0304 allele was previously assigned an erroneous oligotype, because reported oligotyping strategies, Geo, et al., *Hum. Immunol.*, 27:40, 1990 and Lanchbury, et al., *Hum. Immunol.*, 27:136, 1990, could not discriminate a DQB1*0304/DQB1*0303 heterozygote from a DQB1*0301/DQB 1*0302 heterozygote. The differences reflected in Table 2 may be summarized as follows, where the number indicates the amino acid position at which the polymorphism occurs:

TABLE 3

| HLA-DQB1 | 13 | 21 | 26 | 45 | 47 | 57 |
|---|---|---|---|---|---|---|
| 0301 | C | — | TA | A | — | — |
| 0302 | — | — | — | — | T | C |
| 03031 | — | C | — | — | T | — |
| 03032 | — | — | — | — | T | — |
| 0304 | C | — | TA | A | — | C |

Because HLA type is inherited from each parent, an individual may have up to four different HLA-DR alleles. A mixture of 0301 and 0302 will type the same as a mixture of 03032 and 0304 using conventional oligotyping, since each pair taken together contains the same combination of five polymorphisms, and oligotyping cannot reveal linkages between polymorphisms at widely spaced sites using a single probe.

However, sequence specific amplification can be used to resolve which of the alleles is present in such a situation. To determine which of the HLA-DQB1*03 alleles is present, the sample DNA is amplified with primers which selectively amplify HLA-DQB1*03 alleles having the amino acid Y at position 26, namely 0301 and 0304. The amplified DNA is then contacted to a panel of labeled oligonucleotide probes, and typing for C at 57 can then be conducted with the knowledge that the 0302, 03031 and 03032 types are not present, since they were not amplified. In this manner, the two complementary pairs of alleles may be resolved. Table 9 illustrates this.

The same information may, of course, be the basis for typing by negative inference. If sequence-specific amplification fails, indicating that the 0301 and 0304 are not present, further typing may be carried out by any applicable method, such as non-specific amplification of the subject HLA-DR DNA, such as described in the parent application U.S. Ser. No. 07/544,218, filed Jun. 27, 1990, the entire contents of which are incorporated by reference herein, followed by typing using oligonucleotide probes. Again, the problem created by the complementary pairs of alleles has been eliminated.

Typing of the HLA-DRB1*08, *12 and *1404 alleles may be carried out in a manner similar to that for HLA-DQ*03 alleles. HLA-DRB1*08, *12 and *1404 alleles have the sequence 5'-GTACTCTACGGGTGAGTGTT-3' (SEQ ID NO:3) at positions 10–16. Sequence-specific amplification is carried out to obtain DNA which is HLA-DRB1*08, *12 or *1404. Labelled oligonucleotide probes are then used to determine which of the alleles are present in the same manner as described above for HLA-DQ*03. The unrelated allele *1404 is dissimilar from the *08 and *12 alleles in virtually all other polymorphic sites, and may be readily eliminated from consideration if one or more probes for HLA-DRB1*08 and *12 are positive.

As Table 1 shows, there are nine different HLA-DRB1*08 and *12 alleles. Combinations of probes are used to discern the differences between each allele without fear DNA representing another HLA-DRB type having the same polymorphism is also present, since such DNA, if present in the original sample, is not amplified. Specific typing may be based on a positive result for the combination of probes that uniquely identifies the allele, or may be based on negative inference or the process of elimination. For example, negative results on probe combinations associated with eight of the alleles may narrow the possibilities to a single DRB1*08 and *12 allele.

The primers used in the method of the invention amplify intra-locus subsets of HLA alleles. These primers must hybridize with sufficient specificity to limit amplification to the desired targets. The type of amplification procedure is not critical to the invention. For example, PCR or self sustained sequence replication (3SR) may be used. See U.S. Pat. No. 4,683,202 and Fahy et al., *PCR Methods and Applications*, 1:25–33 (1991), the texts of which are incorporated herein in their entireties by reference.

The primer(s) may be labeled or unlabeled, depending on the method used to detect hybrids. Where the hybridization assay uses labeled oligonucleotide probes, the amplified DNA does not need to be labeled in order to detect amplified DNA-oligonucleotide probe hybrids; an unlabeled primer may be utilized. In addition, the primer may be labelled with a label distinguishable from the label attached to the probe, thereby allowing one to monitor the loading of the amplified DNA. Where the hybridization assay uses unlabeled oligonucleotide probes, the amplified DNA can be labeled to detect amplified DNA-oligonucleotide probe hybrids. Thus, in that type of assay, a labeled primer is used to yield labeled amplified DNA.

Table 4 lists the primers used in the present invention to amplify DRB alleles and the sequences which the primers hybridize to. Primer PCR44 selectively amplifies HLA-DRB1*08, *12 and *1404 alleles at positions 10–16. Primers PCR6 and PCR5 hybridize to sequences corresponding to consensus sequences, thereby amplifying all HLA-DRB alleles. Although some polymorphism occurs at HLA-DRB positions 16–22 and 87–94, all known HLA-DRB alleles can be amplified using these primers using appropriate conditions.

Table 5 lists the primers used in the present invention to amplify DQ beta alleles and the sequences which the primers hybridize to. Primer TERVRY.26 (SEQ ID NO:6) hybridizes to an HLA-DQB1 nucleotide sequence corresponding to the amino acid sequence comprising TERVRY (SEQ ID NO:7), thereby selectively amplifying alleles which have the amino acid sequence TERVRY (SEQ ID NO:7), i.e., DQB1*0301, *0304, and *0601 alleles. Primers MCTFTNG.14 (SEQ ID NO:4) and YWNSGK.60 (SEQ ID NO:5) hybridize to sequences corresponding to consensus sequences, thereby amplifying all DQB1 alleles.

bound sequences. See PCT Publication WO 89/1154 to Erlich et al, the text of which is incorporated in its entirety by reference.

In another version of this format, the single strand oligonucleotide probe is labeled, and the sample nucleic acid is unlabeled. After hybridization and washing, the labeled probe, or a labeled fragment of the probe, is released from the membrane and detected to determine if a sequence in the sample hybridized to the labeled oligonucleotide. Release of

TABLE 4

Primers utilized for HLA-DRB1-08/12 oligotyping

| Name | Sequence | SEQ ID NO: | Positive Hybridization | DRB Codons |
|---|---|---|---|---|
| PCR6 | 5'-ATTTCTTCAATGGGACGGAGC-3' | 1 | All DRB Alleles | 16–22 |
| PCR5 | 5'-CGCCGCTGCACTGTGAAGCTCTC-3' | 2 | All DRB Alleles | 87–94 |
| PCR44 | 5'-GTACTCTACGGGTGAGTGTT-3' | 3 | DRB1*08, 12, 1404 | 10–16 |

TABLE 5

Primers utilized for low resolution assays (SEQ ID NOS. 4–6).

| Name | Sequence | Positive Hybrid. | DRB Codons |
|---|---|---|---|
| 5'MCTFTNG.14 | 5'-TGTGCTACTTCACCAACGGG-3' | All DQB1 Alleles | 14–20 |
| 3'YWNSQK.60 | 5'-CCTTCTGGCTGTTCCAGTAC-3' | All DQB1 Alleles | 60–65 |
| 5'TERVRY.26 | 5'-GGACGGAGCGCGTGCGTTAT-3' | DQB1*0301,0304,0601 | 21–26 |

It is generally possible to design a probe sufficiently long to hybridize selectively with the desired HLA-DR or DQ sequence if the sequence is present in a test sample, but not so long that the probe hybridizes in spite of a single base pair mismatch. For this purpose, oligonucleotides ranging from 12 to 25, particularly 12 to 20 nucleic acids in length have proven most successful. The oligonucleotide probes of the invention are used under conditions that detect the presence of the complementary sequences in a nucleic acid derived from a sample. Suitable assay methods for purposes of the present invention to detect hybrids formed are well known in the art.

In one embodiment of the invention, unlabeled amplified HLA DNA is bound to a membrane, the membrane is incubated with a labeled probe under hybridization conditions, unhybridized probe is removed by washing, and the filter is monitored for the presence of hybridized probe. The process is repeated using replicate membranes for each labelled probe. See copending application Ser. No. 07/544,218 and Molkentin et al., Human Immunology, 31:114 (1991) the text of which is incorporated herein in its entirety by reference.

In an alternative format, the amplified target DNA is labeled and the oligonucleotide probes are not labeled. In this format, the unlabeled-single strand oligonucleotide probes capable of hybridization to the selectively amplified DNA are bound to a solid support and exposed single-stranded, labeled target DNA under appropriately stringent hybridization conditions. Unhybridized labeled target DNA is then removed by washing under suitably stringent conditions, and the filter is then monitored for the presence of label can be achieved by digestion with a restriction enzyme that recognizes a restriction site in the duplex hybrid. This procedure, known as oligomer restriction, is described more fully in U.S. Pat. No. 4,683,194 and corresponding EP Patent Publication 164,054, both incorporated herein in their entireties by reference.

The labeled oligonucleotide probes according to the invention comprises a labeling substance which allows a successful hybridization to be detected after non-specifically bound probe (i.e., probe that is not complementary to the target sequence) has been removed, e.g., washed away. Radioactive isotopes such as $^{32}p$ can be readily incorporated as part of the probe. A non-radioactive detection system, e.g., an enzyme-based assay using digoxigenin or biotin as the labeling substance, is most preferred. However, other types of labeling substances, such as fluorescent labels, can also be employed. Numerous methods for preparing labeled oligonucleotide probes are well known.

Table 6 sets forth the sequences of oligonucleotide probes that were designed as part of the present invention to resolve DRB1*08, *12, and *1404 alleles. Table 7 sets forth the sequences of oligonucleotide probes that were designed as part of the present invention to resolve DQB1*03 alleles. Probes were named as the polymorphic amino acid(s) encoded by the segment of the gene complementary to the oligonucleotide and a number corresponding to the position of the polymorphic amino acid(s) in the sequence (e.g., L37L38 detects the nucleotides encoding two leucine residues found at positions 37 and 38 in DRB1*1201 and *1202).

TABLE 6

Oligonucleotide probes utilized for HLA-DRB1-08/12 oligotyping

| Name | Codons | Sequence | SEQ ID NO: | Pos. Hybrid. | Hybrid. Temp. (°C.) | Wash Temp. (°C.) |
|---|---|---|---|---|---|---|
| L37L38 | 36–39 | 5'-CGCAGGACGTCC-3' | 8 | *1201, 1202 | 30 | 32 |
| F37 | 36–39 | 5'-CGCACGAACTCC-3' | 9 | *1404 | 35 | 35 |
| S57 | 56–59 | 5'-CTCGGCGCTAGG-3' | 10 | *0801, *0803, *0805 | 30 | 30 |
| con61[a] | 61–64 | 5'-TCTGGCTGTTCC-3' | 11 | All DRB | 30 | 30 |
| I67 | 67–71 | 5'-CCTGTCTTCCAGGATG-3' | 12 | *0803, 1201 | 35 | 55 |
| F67 | 67–71 | 5'-CTGTCTTCCAGGAAG-3' | 13 | *0801, 0802, 0804, 0805, 1202 | 35 | 45 |
| A74 | 70–74 | 5'-CGCGGCCCGCCTGT-3' | 14 | *0805 | 30 | 48 |
| L74 | 71–74 | 5'-CAGGGCCCGCCT-3' | 15 | *0801, 0802, 0803, 0804 | 30 | 32 |
| G86 | 85–88 | 5'-CTCTCACCAACC-3' | 16 | *0801, 0802, 0803, 0805 | 30 | 32 |
| V86 | 85–88 | 5'-CTCTCCACAACC-3' | 17 | *1404, 0804 | 30 | 32 |

[a]con61 is a consensus probe.

TABLE 7

| Name | Codons | Sequence | SEQ ID NO: | Pos. Hybrid (DQB1*) | Hybrid. Temp. (°C.) | Wash Temp. (°C.) |
|---|---|---|---|---|---|---|
| QGRP.53 | 53–56 | 5'-GGCCGCCCCTGC-3' | 18 | 05**, 06** | 33 | 33 |
| GEFR.46 | 45–48 | 5'-CGGAACTCCCCC-3' | 19 | 0201 | 33 | 33 |
| LGPP.55 | 53–56 | 5'-AGGCGGCCCCAG-3' | 20 | 03** | 33 | 33 |
| RLDA.56 | 55–58 | 5'-GCGTCAAGCCGC-3' | 21 | 04** | 33 | 33 |
| EVYR.45 | 45–48 | 5'-CGGTACACCTCC-3' | 22 | 0301, 0304 | 33 | 33 |
| PPAA.57 | 55–58 | 5'-GGCGGCAGGCGG-3' | 23 | 0302, 0304 | 35 | 42 |
| PPDA.57 | 55–58 | 5'-CGGCGTCAGGCG-3' | 24 | 0301, 0303 | 33 | 33 |
| LVRG.23 | 23–26 | 5'-CCCCGCACGAGC-3' | 25 | 0401 | 33 | 33 |
| GVYR.47 | 45–48 | 5'-CGATACACCCCC-3' | 26 | 0302, 0303, 0503, 0601 | 33 | 33 |

Table 8 describes the hybridization patterns corresponding to HLA-DRB1*08, *12, and *1404 alleles using primers PCR44 and PCR5, and Table 9 describes the hybridization patterns corresponding to HLA DQB1*02–06 alleles.

TABLE 8

| Probe | Oligotype | | | | | | | |
|---|---|---|---|---|---|---|---|---|
|  | 0805 | 0801 | 802 | 0804 | 0803 | 1404 | 1201 | 1202 |
| L37–L38 | – | – | – | – | – | – | + | + |
| F37 | – | – | – | – | – | + | – | – |
| S57 | + | + | – | – | + | – | – | – |
| con61 | + | + | + | + | + | + | + | + |
| I67 | – | – | – | + | – | – | + | – |
| F67 | + | + | + | + | – | – | – | + |
| A74 | + | – | – | – | – | – | – | – |
| L74 | – | + | + | + | + | – | – | – |
| G86 | + | + | + | – | + | – | – | – |
| V86 | – | – | – | + | – | + | – | – |

TABLE 9

| Probe | DQB1 oligotype | | | | | | | |
|---|---|---|---|---|---|---|---|---|
|  | -05**, -06** | -0201 | -0301 | -0302 | -0303 | -0304 | -0401 | -0402 |
| QGRP.53 | + | – | – | – | – | – | – | – |
| GEFR.46 | – | + | – | – | – | – | – | – |
| LGPP.55 | – | – | + | + | + | + | – | – |
| RLDA.56 | – | – | – | – | – | – | + | + |
| EVYR.45 | – | – | + | – | – | + | – | – |
| PPAA.57 | – | – | – | + | – | + | – | – |
| PPDA.57 | – | – | + | – | + | – | – | – |
| LVRG.23 | – | – | – | – | – | – | + | – |
| GVYR.47 | (+) | – | – | + | + | – | + | + |
| RFDS.39 | + | + | + | + | + | + | + | + |

(+) indicates that some but not all DQB1-05 and DQB1-06 oligotypes are positive for GVYR.47

HLA typing of DRB1*08 and *12 and DQB1*03 alleles can be carried out by following a one or two step process. In the two step process, the first step comprises using techniques known in the art to determine whether the sample is positive for HLA-DRw8, DRw12, DRw14 or DQw3 serotypes, or oligotypes corresponding to those serotypes. The second step, provided that the sample is positive for the aforementioned serotypes or oligotypes corresponding to those serotypes, comprises selectively amplifying the sample with intra-locus specific probes according to the invention and thereafter hybridizing the amplified sample with a plurality of probes according to the invention. In the one step process, the first "prescreening step" described immediately above is omitted.

For example, to determine which of the HLA-DRB1*08 or *12 alleles is present in the sample, the sample DNA is amplified with primers which selectively amplify alleles having the characteristic sequence at positions 10–16. The amplified DNA is then contacted to a panel of labeled oligonucleotide probes listed in Table 6. The alleles present in the sample are identified by comparing the hybridization pattern with the hybridization patterns listed in Table 8. The order of steps may even be reversed, so that SSA is the final step that resolves a specific allele based on a prior series of oligonucleotide probe hybridizations.

Similarly, to determine which of the HLA-DQB1*03 alleles is present, the sample DNA is amplified with primers which selectively amplify HLA-DQB1*03 alleles having the amino acid sequence TERVRY at positions 21–26. The amplified DNA is then contacted to a panel of labeled oligonucleotide probes listed in Table 7, although only probes PPAA.57 and PPDA. 57 are required to resolve the *0301 and *0304 alleles. The alleles present in the sample are identified by comparing their hybridization pattern with the hybridization patterns listed in Table 9.

A number of examples of the present invention, which are provided only for illustrative purposes and not to limit the scope of the invention, are presented below. In the following examples, oligonucleotides were synthesized using either a Gene Assembler (Pharmacia Fine Chemicals, Piscataway, N.J.) or a PCR Mate (Applied Biosystems, Foster City, Calif.). The sequences of all primers and probes used in this study are provided in the tables set forth in the specification.

EXAMPLE 1—IDENTIFICATION OF HLA-DRB1-08 AND 12 ALLELES

A. DNA Isolation

Genomic DNA was isolated using a standard procedure described in Miller et al, *Nucleic Acids Res.*, 16:1205, 1988, from B-Lymphoblastoid cell lines or white blood cells that were typed as HLA-DRw8 and -DRw12 using known serological methods, Van Rood J J, et al. *Tissue Antigens* 5:73, 1975.

B. Amplification

The isolated DNA described in paragraph A. was amplified using the PCR as described in Molkentin, et al., *Hum. Immunol.*, 31:114, 1991, with the modifications described below. Intralocus-specific amplification utilized a 5' primer (PCR44) complementary to sequences corresponding to 5'-GTACTCTACGGGTGAGTGTT-3' (SEQ ID NO:3) at positions 10–16 and a 3' primer (PCR5) complementary to codons 87–94 of all HLA-DRB alleles; $MgCl_2$ was 3.5mM; and thermal cycling was 20 seconds at 98° C., 30 seconds at 55° C., 30 seconds at 72° C.

C. Labeling of Oligonucleotide Probes

Probes listed in Table 6 were labeled using digoxigenin-11-dUTP as described in Molkentin, et. al. *Human Immunology* 31:114, 1991.

D. Hybridization

The amplified DNA was contacted to a panel of digoxigenin labeled oligonucleotide probes listed in Table 6, using temperatures for probe hybridizations and washes that are listed in Table 6. More specifically, hybridization of the amplified DNA to a panel of 10 nonradioactive probes listed in Table 6 permitted assignment of a unique oligotype to each reported allele in this group, i.e., HLA-DRB1*0801, *0802, *0803, *0804, *0805, *1404, *1201, and *1202. See Table 8. An additional allele, HLA-DRB1*1404, assigned an "HLA-DRw8-like" serological specificity, classified as a member of the HLA-DRB1*14 group, was also amplified using primers PCR44 and PCR5 and detected in this assay.

For the HLA-DRB1*08, *12, and *1404 alleles, oligotypes were assigned based upon the specific pattern of hybridization listed in Table 8. For example, DRB1-0801 oligotype was assigned if the amplified DNA hybridized with S57, F67, L74, G86, but not to the remaining probes (i.e., L37L38, F37, I67, A74, V86). Likewise, DRB1-1201 oligotype was assigned if hybridization was positive for L37L38 and I67 and negative for F37, S57, F67, A74, L74, G86, V86.

Internal controls used to monitor the specificity of each hybridization were amplified using primers PCR6 and PCR5 which are specific for all HLA-DRB alleles. A consensus probe designated con61, which hybridizes to all HLA-DRB alleles was included to monitor the amount of DNA bound to the membrane. The hybridization pattern obtained is described in Table 8 as well as the identity of the alleles present in the sample.

E. Discovery of New Allele

Hybridization patterns presented by an allele, designated as HLA-DRB1*0805, contains a combination of polymorphic sequences that are not consistent with any previously reported alleles. Sequence analysis of the exon encoding the first domain of DRB1-0805 confirmed that the sequence of that allele had not been previously reported.

F. Nucleotide Sequencing of Alleles

The HLA-DRB1*08/12/1404 specific 5' primer (PCR44) was utilized to selectively amplify the second exon (codons 10–94) of the HLA-DR alleles. Amplified DNA was ligated into the PCR1000 vector (Invitrogen Corporation, San Diego, Calif. Plasmid DNA was isolated from clear colonies and sequences of the inserts from multiple clones were determined using vector primers and standard dideoxy termination methods. Sanger et al, P.N.A.S., 74:5463, (1977).

EXAMPLE 2—IDENTIFICATION OF HLA-DQB1-03 ALLELES

A. DNA Isolation

Genomic DNA was isolated using a standard procedure described in Miller et. al., *Nucleic Acids Res* 16:1205, 1988, from B-lymphoblastoid cell lines or white blood cells that were typed as HLA-DQw3 using known serological methods, Van Rood J J, et al. *Tissue Antigens* 5:73, 1975.

B. Amplification

The isolated DNA described in paragraph A was amplified using the PCR as described in Molkentin, et al., *Hum. Immunol.*, 31:114, 1991, with the modifications described below. Intralocus-specific amplification utilized a 5' primer (5'TERVRY.26) complementary to sequences corresponding to TERVRY at positions 21–26 and a 3' primer (3'YWN-SKQ.60) complementary to codons 60–65 of all HLA-DQB1 alleles; $MgCl_2$ was 1.5mM; and thermal cycling was 15 seconds at 98° C., 20 seconds at 65° C., 15 seconds at 72° C. Thirty cycles were carried out for each amplification. Locus-specific amplification utilized a 5' primer (5'MCY-FTNG.14) which is complementary to most nucleotides at codons 14–20 of all HLA-DQB1 alleles and 3'YWN-SQK.60; $MgCl_2$ was 1.5 mM; and thermal cycling was 15 seconds at 98° C., 20 seconds at 55° C., 15 seconds at 72° C. for 30 cycles, with a 7 minute 72° C. final extension.

C. Labeling of Oligonucleotide Probes

Probes listed in Table 7 were labeled using digoxigenin-11-dUTP as described in Molkentin, et. al. *Human Immunology* 31:114, 1991.

D. Hybridization

The amplified DNA was contacted to a panel of digoxigenin-labeled oligonucleotide probes listed in Table 7, using temperatures for probe hybridizations and washes that are listed in Table 7. More specifically, hybridization of the amplified DNA to a panel of 9 nonradioactive probes listed in Table 7 permitted assignment of a unique oligotype to each reported allele in this group except for DQB1*05 and DQB1*06 alleles which require additional testing for complete resolution as described in Molkentin, et. al., *Human Immunology* 31:114, 1991. Therefore the alleles HLA-DQB1-0201, 0301, 0302, 0303, 0304, 0401 and 0402 could be specifically identified. DQB1*05 and DQB1*06 alleles could be detected but not resolved into specific alleles. See Table 9.

For the HLA-DQB1 alleles, oligotypes were assigned based upon the specific pattern of hybridization listed in Table 9. For example, if serological or preliminary oligotyping identified an individual as either a DQB1*0301/,0302 or DQB1*0303/,0304 heterozygote, the intra-locus amplification was performed. A DQB1- 0301/0302 oligotype was assigned if the intra-locus amplified DNA hybridized with LGPP.55, EVYR.45, and PPDA.57 but not to the remaining probes (i.e., QGRP.53, GEFR.46, PPAA.57, RLDA.56, LVRG.23, GVYR.47), indicating the presence of the DQB1*0301 allele and the absence of the DQB1*0304 allele. Likewise, the DQB1-0303/-0304 oligotype was assigned if, following the intra-locus amplification, hybridization was positive for LGPP.55, EVYR.45, and PPAA.57, and negative for QGRP.53, GEFR.46, RLDA.56, PPDA.57, LVRG.23 and GVYR.47.

Internal controls used to monitor the specificity of each hybridization were amplified using primers 5'MCYFTNG.14 and 3'YWNSQK.60 which are specific for HLA-DQB1 alleles. A consensus probe designated RFDS.39, which hybridizes to all HLA-DQB1 alleles was included to monitor the amount of DNA bound to the membrane. The hybridization pattern obtained is described in Table 9 as well as the identity of the alleles present in the sample.

E. Discovery of New Allele

Hybridization patterns presented by an allele, designated as DQB1*0304, contains a combination of polymorphic sequences that are not attributable to any previously reported allele. Determination of the nucleotide sequence of the second exon of DQB1*0304 confirmed a sequence that had not been previously reported.

F. Nucleotide Sequencing of Alleles

Total cellular RNA was isolated from peripheral blood leukocytes as described by Chirgwin et. al., *Biochemistry* 18:5294, 1979. cDNA was synthesized and the HLA-DQB1 locus was enzymatically amplified using two primers complementary to untranslated regions of all HLA-DQB1 alleles. The sequence of the 5' primer (DQB 5'UT, SEQ ID NO:27) was 5'-CAGGTACATCAGATCCATCAGG-3' The sequence of the 3' primer (DQB 3'UT, SEQ ID NO:28) was 5'-CAGGTGGGAATTCTGGGCAGGG-3'. The amplified fragment was ligated into pCR1000 (Invitrogen, San Diego, Calif.) and introduced into *E. coli* by transformation. Transformants were selected for kanamycin resistance and screened for the presence of an insert of the appropriate size. Nucleotide sequences of the first domain of three independent cDNA inserts were determined using vector primers and standard dideoxy termination methods. Sanger et al, *P.N.A.S.*, 74:5463 (1977).

While the invention has been described in detail and with reference to specific embodiments thereof, various changes and modifications can be made therein without departing from the spirit and scope thereof. In the sequence listing which follows, the amino acids for HLA-DR sequences have been renumbered starting from 1. However, in the preceding specification, the art-recognized numbering starting at 6 has been used.

I claim:

1. A method of HLA typing a sample for an unknown pair of alleles, which unknown pair is one of a first or second pair of alleles of a known basic HLA allele type, wherein the second pair of alleles contains a set of HLA polymorphisms which are the same as the first pair, the polymorphisms of the set being divided between each of the first and second pairs of alleles such that the polymorphisms of the set found in the first member of each pair are not found in the second member of each pair, and the polymorphisms of the set found in the second member of each pair are not found in the first member of each pair, but some of which polymorphisms are located on a different allele of the second pair compared to the first pair so that the second pair of alleles is different from the first pair, which method comprises:

selectively amplifying one of the unknown pair of alleles such that DNA of the other allele of the unknown pair is not amplified;

analyzing the amplified DNA to determine which polymorphisms of the set common to the first and second pairs are present; and determining whether the first or second pair of alleles is present in the sample.

2. The method of claim 1, wherein the selective amplification step comprises a polymerase chain reaction.

3. The method of claim 2, wherein the selective amplification utilizes a primer effective, under hybridizing conditions, to cause sequence-specific amplification of an allelic polymorphism common to only one member of the first and second pairs of alleles.

4. The method of claim 1, wherein the amplified DNA is analyzed by oligonucleotide probe hybridization.

5. The method of claim 1, further comprising:

contacting amounts of the amplified DNA with a panel of labeled oligonucleotide probes under hybridizing conditions, which probes specifically hybridize with sequences containing allelic polymorphisms of the set found in the first and second pairs of alleles, other than the polymorphism which was used in the sequence-specific amplification;

detecting the formation of DNA duplexes by the labelled probes and the amounts of amplified DNA; and determining whether the first or second pair of alleles is present in the sample from the probe hybridization results.

6. The method of claim 1, wherein one of the first and second pairs is DQB1*0304/DQB1*03032 and the other is DQB1*0301/DQB1*0302.

7. A method of HLA typing a sample for an unknown pair of alleles, which unknown pair is one of a first or second pair of alleles of a known basic HLA allele type, wherein the second pair of alleles contains a set of HLA polymorphisms which are the same as the first pair, the polymorphisms of the set being divided between each of the first and second pairs of alleles such that the polymorphisms of the set found in the first member of each pair are not found in the second member of each pair, and the polymorphisms of the set found in the second member of each pair are not found in the first member of each pair, but some of which polymorphisms are located on a different allele of the second pair compared to the first pair so that the second pair of alleles is different from the first pair, which method comprises:

selectively amplifying one of the unknown pair of alleles such that DNA of the other allele of the unknown pair is not amplified using a primer effective, under hybridizing conditions, to cause sequence-specific amplification of an allelic polymorphism common to only one member of each of the first and second pairs of alleles;

contacting amounts of the selectively amplified DNA with a panel of labeled oligonucleotide probes under hybridizing conditions, which probes specifically hybridize with sequences containing allelic polymorphisms found in the set of polymorphisms of the first and second pairs of alleles;

detecting the formation of DNA duplexes by the labelled probes and the amounts of amplified DNA; and determining whether the first or second pair of alleles is present in the sample from the probe hybridization results.

8. The method of claim 7, wherein the selective amplification step comprises a polymerase chain reaction.

9. The method of claim 8, wherein one of the first and second pairs is DQB1*0304/DQB1*03032 and the other is DQB1*0301/DQB1*0302.

10. In a method of HLA typing which includes the steps of determining the HLA type of a tissue sample and comparing the result with known HLA types, the improvement which comprises:

determining if the tissue sample is DQB1*03304.

11. In a method of HLA typing which includes the steps of determining the HLA type of a tissue sample and comparing the result with known HLA types, the improvement which comprises:

determining if the tissue sample is HLA-DRB1*0805.

* * * * *